(12) United States Patent
Moon

(10) Patent No.: US 7,542,797 B2
(45) Date of Patent: Jun. 2, 2009

(54) ELECTROTHERAPY APPARATUS USING LOW AND INTERMEDIATE FREQUENCIES

(76) Inventor: Myung-Kun Moon, 3 Mogdong Apt., 310 Dong 802 Ho, Mog 5 Dong, Yangcheongu, Seoul 158-753 (KR)

( * ) Notice: Subject to any disclaimer, the term of this patent is extended or adjusted under 35 U.S.C. 154(b) by 383 days.

(21) Appl. No.: 10/543,829

(22) PCT Filed: Jun. 2, 2003

(86) PCT No.: PCT/KR03/01082

§ 371 (c)(1), (2), (4) Date: May 11, 2006

(87) PCT Pub. No.: WO2004/067084

PCT Pub. Date: Aug. 12, 2004

(65) Prior Publication Data

US 2006/0247730 A1 Nov. 2, 2006

(30) Foreign Application Priority Data

Jan. 30, 2003 (KR) .................. 10-2003-0006076

(51) Int. Cl.
*A61N 1/00* (2006.01)
(52) U.S. Cl. .......................................................... 607/2
(58) Field of Classification Search ................ 607/1, 607/2, 60, 72, 63
See application file for complete search history.

(56) References Cited

U.S. PATENT DOCUMENTS

| 3,534,733 | A | * | 10/1970 | Phipps et al. ............... 600/387 |
| 5,146,920 | A | | 9/1992 | Yuuchi et al. |
| 6,212,432 | B1 | | 4/2001 | Matsuura |
| 6,445,955 | B1 | | 9/2002 | Michelson et al. |
| 2002/0147466 | A1 | * | 10/2002 | Bernabei ...................... 607/3 |

FOREIGN PATENT DOCUMENTS

| JP | 05-165 | 10/1994 |
| JP | 2002-291913 | 10/2002 |
| JP | 2003-10344 | 1/2003 |
| KR | 20-0286105 | 8/2002 |

* cited by examiner

*Primary Examiner*—Scott M Getzow
(74) *Attorney, Agent, or Firm*—Staas & Halsey LLP

(57) ABSTRACT

Disclosed herein is an electrotherapy apparatus using low and intermediate frequencies. In the electrotherapy apparatus of the present invention, a user selects one of low and intermediate output modes depending upon need, positive and negative electrodes made of conductive rubber are provided therein, and a vacuum cup is attached to the body. Accordingly, the electrotherapy apparatus of the present invention can be used semi-permanently, the ill side-effects thereof can be prevented, and the desired effects thereof can be maximized.

2 Claims, 7 Drawing Sheets

ELECTROTHERAPY APPARATUS USING LOW AND INTERMEDIATE FREQUENCIES

TECHNICAL FIELD

The present invention relates, in general, to an electrotherapy apparatus using low and intermediate frequencies and, more particularly, to an electrotherapy apparatus using low and intermediate frequencies, which outputs low and intermediate frequencies modulated in such a way that the intermediate frequency is carried on the low frequency depending on the need of a user, and is adapted to be attached to a human body using air compression.

BACKGROUND ART

Generally, electrotherapy uses a low frequency of 1 Hz to 300 Hz. A low-frequency electrotherapy apparatus stimulates the skin of a human, and is expected to exhibit a massage effect. Accordingly, the low-frequency electrotherapy apparatus has been effectively used for a recovery from fatigue by persons who have muscle pains after exercising, feel neck, arm or leg pains due to long drives, and have insomnia due to hypersensitivity.

A conventional electrotherapy apparatus is attached to a human body using an electrode pad, but the electrode pad is disposable, so that the use of the electrode pad is inconvenient in that the electrode pad needs to be replaced with a new one because the adhesive power thereof is reduced after use several times. Additionally, when the electrode pad is detached from the human body, the electrode pad causes a user not only an allergy due to stimulation to the human body but also considerable rejection due to a phenomenon in which the roots of hair are pulled out.

Furthermore, it was difficult to expect a wide treatment effect because the conventional electrotherapy apparatus uses only a low frequency whose effect is limited to massages.

DISCLOSURE OF THE INVENTION

Accordingly, the present invention has been made keeping in mind the above problems occurring in the prior art, and an object of the present invention is to provide an electrotherapy apparatus using low and intermediate frequencies, which can perform a treatment using a frequency selected by a user depending on need from low and intermediate frequencies, which are modulated in such a way that the intermediate frequency is carried on the low frequency, can be attached to a human body using air compression without ill side-effects, such as an allergy, and has a lengthy life span.

The above-described object can be achieved by attaching the electrotherapy apparatus, which outputs the low and intermediate frequencies to the human body, using an air compression method capable of exhibiting the effect of a cupping glass, which is an oriental-medical appliance, and using conductive rubber as an electrode-pad that comes in contact with the human body.

With reference to the attached drawings, the technical construction of the electrotherapy apparatus using low and intermediate frequencies is described below.

In order to accomplish the above object, the present invention provides an electrotherapy apparatus using low and intermediate frequencies, including a vacuum cup 10 to be attached to a human body, a housing 20 connected to an upper portion of the vacuum cup 10, a connection member 30 adapted to connect the vacuum cup 10 and the housing 20, a frequency generator 40 on a printed circuit board that is included in the housing 20 and includes circuits including a sensor 41 and a microcomputer 430, negative and positive electrode plates 50 and 51 contained in the vacuum cup 10 to be supported by springs S1 and S2, and adapted to come in contact with the human body while being operated to ascend and descend, connection terminals 60 and 61 connected to the frequency generator 40 and the springs S1 and S2 to output frequencies to the negative and positive electrode plates 50 and 51, a connection terminal 70 located in the vacuum cup 10 to be connected to the sensor 41 so as to operate the frequency generator 40 during treatment, and a remote controller 80 adapted to wirelessly control the frequency generator 40.

In this case, the negative and positive electrode plates 50 and 51 may be connected to each other through an insulation plate 520, and include fixation protrusions 500 and 510 on which the springs S1 and S2 are fixed, respectively.

The springs S1 and S2 may be formed of coil springs, and a diameter of each of the springs S1 and S2 may increase in a direction from the upper and lower ends thereof to a center portion thereof.

The frequency generator 40 may include a receiving unit 410 receiving a control signal of the remote controller 80, a current detection unit 420 detecting the magnitude of currents and giving notice that the negative and positive electrode plates 50 and 51 are detached from the human body, a microcomputer 430 cutting off power in response to a signal of the current detection unit 420, and controlling output frequency and voltage in response to a control signal of the receiving unit 410, a frequency adjustment unit 440 amplifying the low and intermediate frequencies, which are modulated and output in such a way that the intermediate frequency is carried on the low frequency, according to an internal program of the microcomputer 430, and a frequency output unit 450 outputting the low and intermediate frequencies amplified in the frequency adjustment unit 440.

BEST MODE FOR CARRYING OUT THE INVENTION

Figure 1:
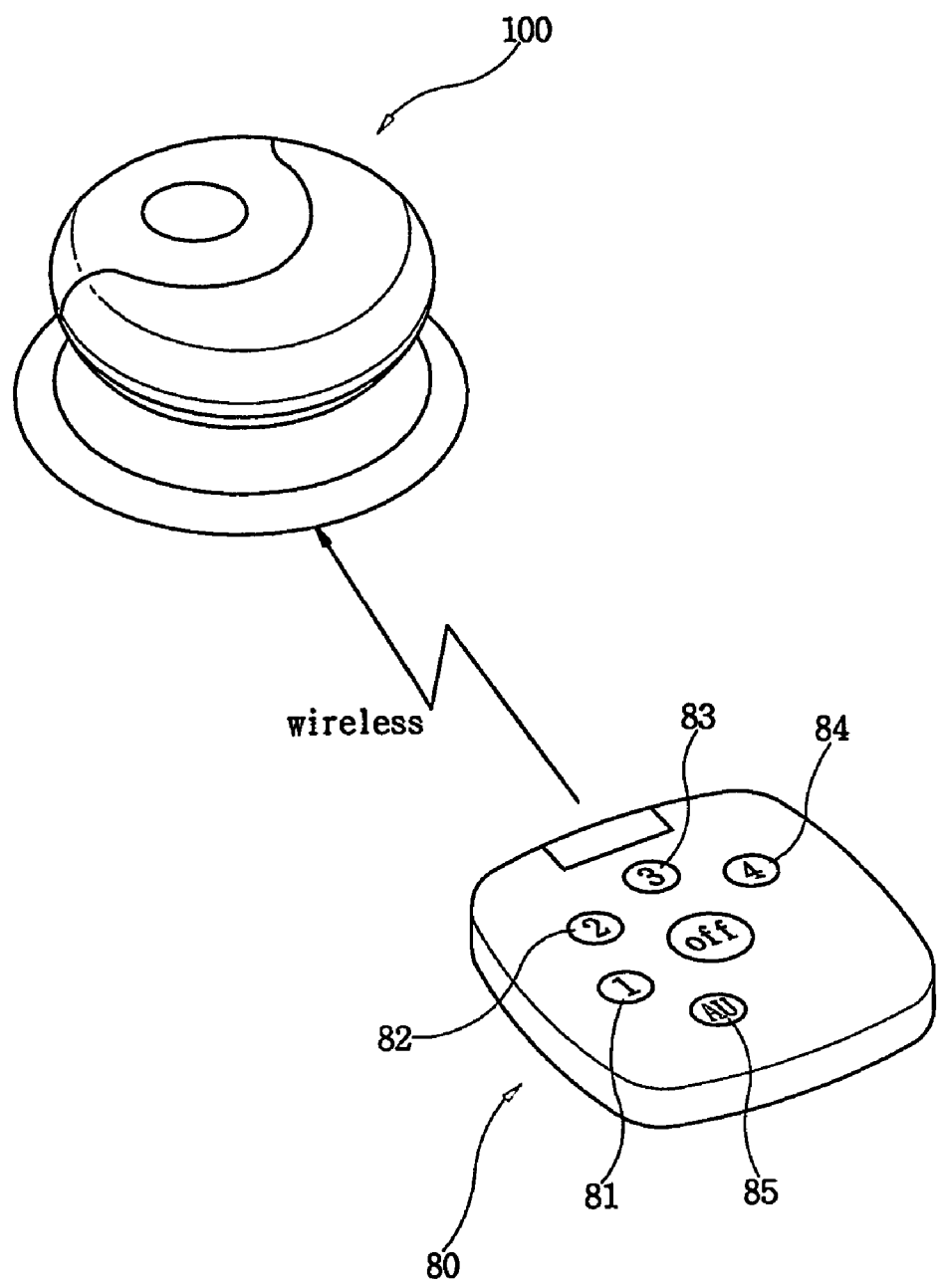
FIG. 1 is a perspective view of an electrotherapy apparatus using low and intermediate frequencies according to the present invention.

FIG. 1 is a perspective view of an electrotherapy apparatus using low and intermediate frequencies according to the present invention.

FIG. 1 shows a remote controller 80 allowing a user to input selected signals through an off switch "off" and other switches 81 to 85, and the electrotherapy apparatus 100 using low and intermediate frequencies, which outputs low and intermediate frequencies modulated in such a way that the intermediate frequency is carried on the low frequency in response to a control signal received from the remote controller 80.

Figure 2:
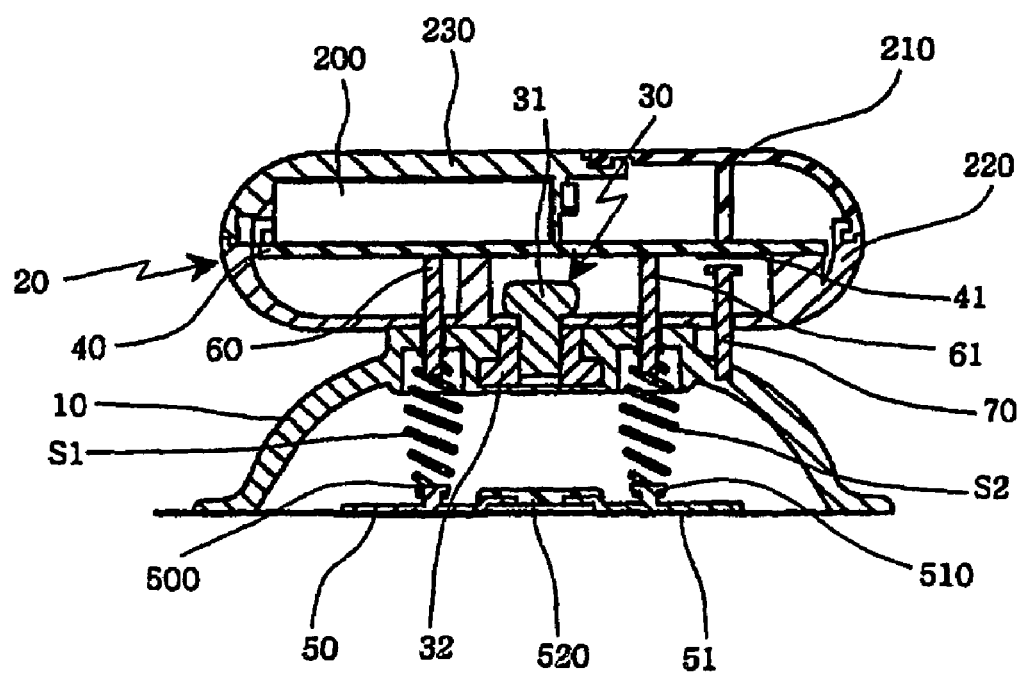
FIG. 2 is a longitudinal section of the electrotherapy apparatus of the present invention.

FIG. 2 is a longitudinal section of the electrotherapy apparatus of the present invention.

The electrotherapy apparatus 100 of the present invention includes a vacuum cup 10 attached to a human body, a housing 20 connected to the upper portion of the vacuum cup 10, a connection member 30 adapted to connect the vacuum cup 10 and the housing 20, a frequency generator 40 on a printed circuit board that is included in the housing 30 and includes circuits including a sensor 41 and a microcomputer 430, negative and positive electrode plates 50 and 51 contained in the vacuum cup 10 to be supported by springs S1 and S2 and brought into contact with a human body while being operated to ascend and descend, connection terminals 60 and 61 connected to the frequency generator 40 and the springs 60 and 61 to output frequencies to the negative and positive electrode plates 50 and 51, and a contact terminal 70 placed on the vacuum cup 10 to be connected to the sensor 41 to operate the frequency generator 40 at the time of treatment.

The vacuum cup 10 is made of antibacterial rubber to be sanitarily attached to the human body.

The housing 20 is formed by combining an upper housing 210, including a battery 200 and the frequency generator 40 therein, with a lower housing 220.

The upper housing 210 includes a cover 230 on a portion thereof to remove the battery 200 contained therein.

The connection member 30 includes a connection part 31 and a fixation part 32 to connect the vacuum cup 10 and the housing 20.

The negative and positive electrode plates 50 and 51 are connected to each other through an insulation plate 520, and include fixation protrusions 500 and 510 to which the springs S1 and S2 are fixed, respectively.

The springs S1 and S2 are formed of coil springs to allow the electrotherapy apparatus to come in close contact with the skin. Additionally, the springs S1 and S2 are configured in such a way that the diameter of each of the springs S1 and S2 increases in a direction from the upper and lower ends thereof to a center portion thereof, so that the springs S1 and S2 are not bent and enable the air contact portion thereof to be increased, and thus the adhesive power thereof is increased.

Figure 3:
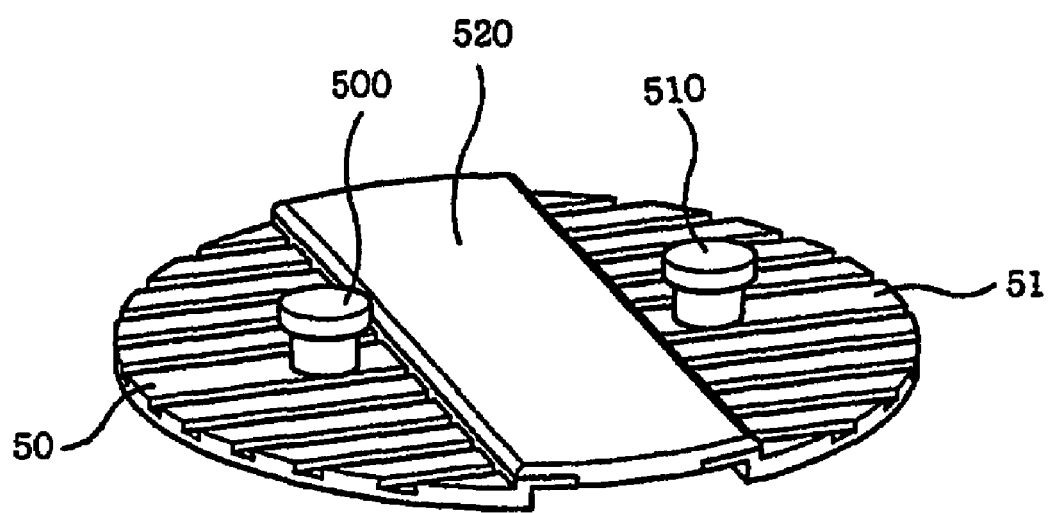
FIG. 3 is a perspective view of the negative and positive electrode plates of the present invention.

FIG. 3 is a perspective view showing the negative and positive electrode plates of the present invention.

The negative and positive electrode plates 50 and 51 apply frequencies to a human body, are connected to each other through the insulation plate 520, and include the fixation protrusions 500 and 510 thereon to allow the springs S1 and S2 to be connected thereto, respectively.

Additionally, the negative and positive electrode plates 50 and 51 are made of conductive rubber (silicon), and processed to be antibacterial. Accordingly, the negative and positive electrode plates 50 and 51 can be used cleanly and semipermanently, and be flexibly attached to the curved part of the human body.

Figure 4:
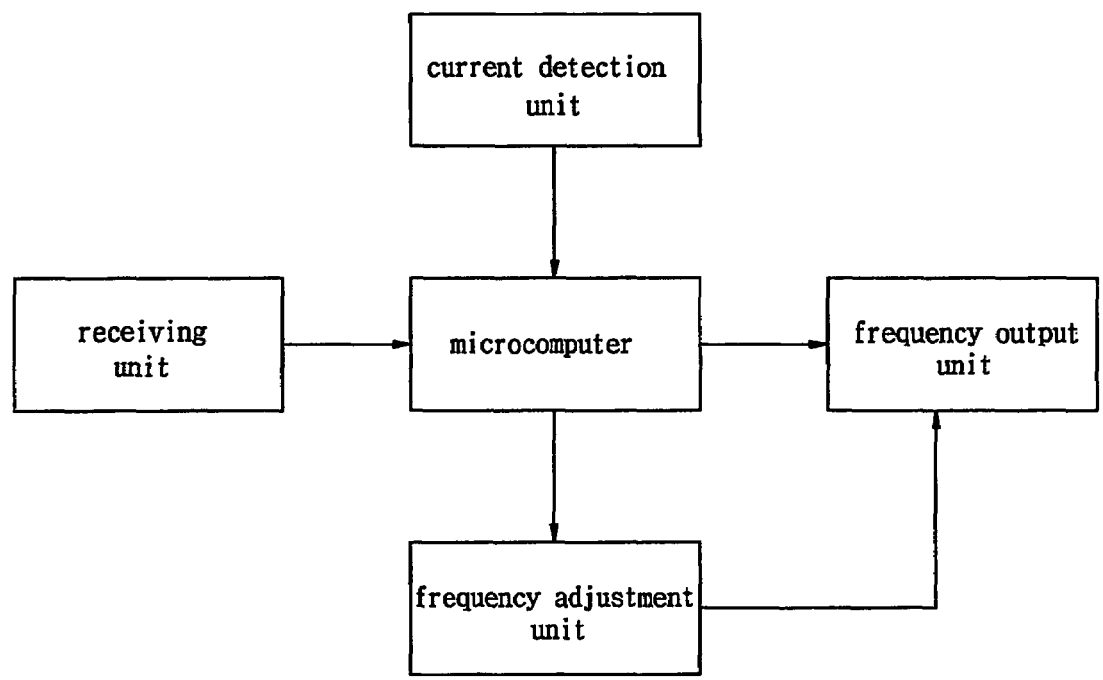
FIG. 4 is a block diagram of the frequency generator of the present invention.

FIG. 4 is a block diagram of the frequency generator of the present invention.

As shown in FIG. 4, the frequency generator 40 includes a receiving unit 410 receiving the signal of the remote controller 80, a current detection unit 420 monitoring the magnitude of currents and giving notice that the negative and positive electrode plates 50 and 51 are detached from the human body, a microcomputer 430 cutting off power in response to the signal of the current detection unit 420, and controlling an output frequency and voltage in response to a signal from the receiving unit 410, a frequency adjustment unit 440 amplifying low and intermediate frequencies, which are modulated in such a way that the intermediate frequency is carried on the low frequency by the internal program of the microcomputer 430, and a frequency output unit 450 outputting the low and intermediate frequencies amplified in the frequency adjustment unit 440.

The receiving unit 410 receives a selected signal, which is input and transmitted through the remote controller 80 by a user.

Based on the fact that the electrotherapy apparatus 100 performs therapy using a minute current existing in human bodies, the current detection unit 420 monitors current, and informs the microcomputer 430 that the electrotherapy apparatus 100 is detached from the human body when the current is changed because the electrotherapy apparatus 100 is detached from the human body.

The microcomputer 430 cuts off power supply to the frequency generator 40 of the present invention in response to the signal of the current detection unit 420. Additionally, in response to the signal from the receiving unit 410, the microcomputer 430 turns off the power or outputs low and intermediate frequencies, which are modulated in such a way that the intermediate frequency is carried on the low frequency, not to shock to the human body at regular periods according to a pre-input program.

The frequency adjustment unit 440 amplifies voltage values of the low and intermediate frequencies output from the microcomputer 430.

The frequency output unit 450 alternatively transmits the low and intermediate frequencies, which are transmitted from the microcomputer 430 through the frequency adjustment unit 440, to the negative and positive electrode plates 50 and 51 through the connection terminals 60 and 61, respectively.

Figure 5:
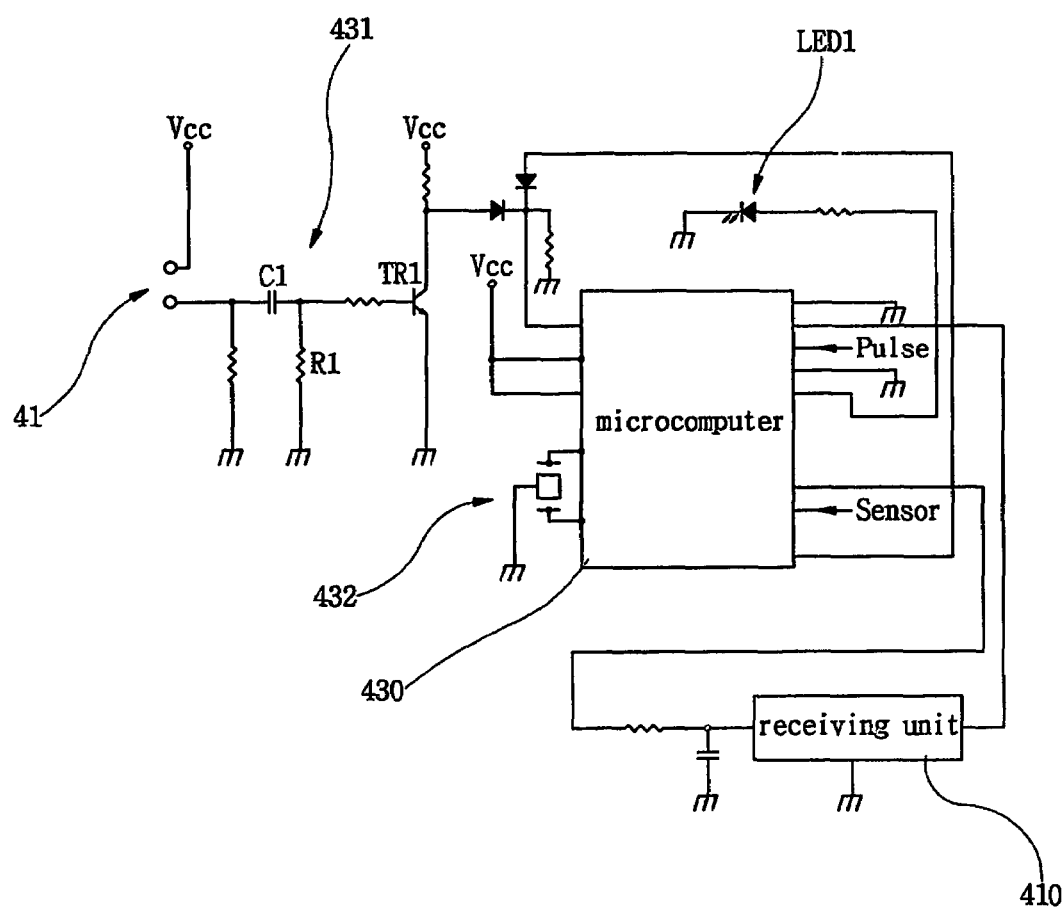
FIGS. 5 and 6 are circuit diagrams showing the constructions of the frequency generator of the present invention in detail.
Figure 6:
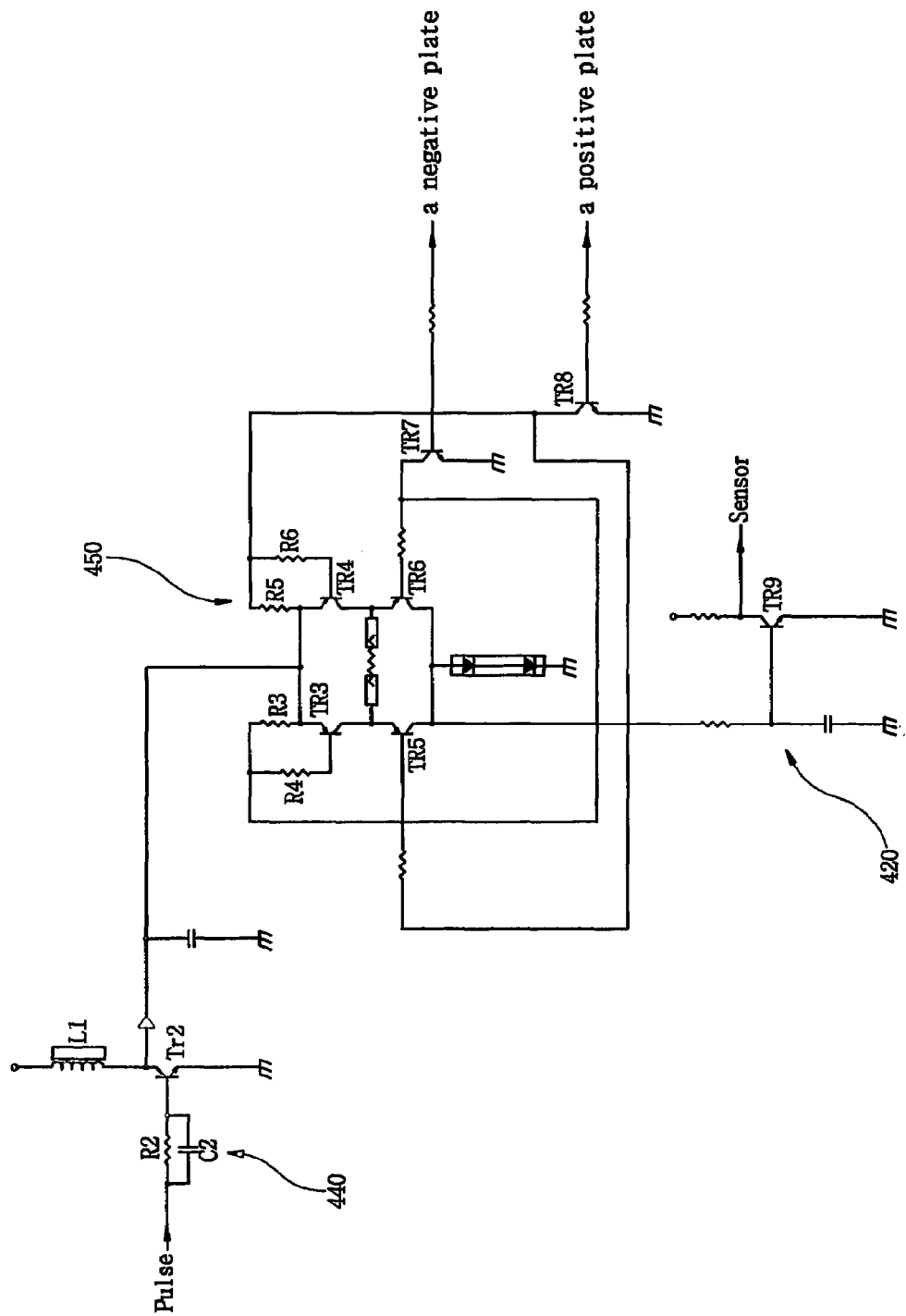

FIGS. 5 and 6 are views showing the construction of the frequency generator of the present invention in detail.

By a sensor 41 turned on by a contact terminal 70, a transistor TR1 is turned on while operating power $V_{cc}$ is charged and discharged in and from a condenser C1 while passing through a time-constant device 431 formed of the condenser C1 and a resistor R1.

A single pulse, which has a "L" value only while the transistor TR1 is turned on, is applied to the microcomputer 430, so that the microcomputer 430 is in a standby mode.

In this case, the microcomputer 430 in the standby mode detects whether there is a signal input by the remote controller 80 through the receiving unit 410. If, as a result of the detection, there is no signal input through the receiving unit 410 for some seconds, the microcomputer 430 enters a sleep mode to reduce the consumption of a battery 200.

To return to the standby mode from the sleep mode, the contact terminal 70 should be pushed once so that another single pulse is applied to the microcomputer 430.

In the case where the microcomputer 430 is in a standby mode, the microcomputer 430 informs an outside of the state, in which the microcomputer 430 can receive a signal from the remote controller 80, by flickering a light emitting diode LED1.

The microcomputer 430 in the standby mode monitors whether a signal based on the selection of the user is input through the remote controller 80 while being supplied with the power of the battery 200.

If, as a result of the detection, there is a signal input through the remote controller 80, the microcomputer 430 determines which one of the off switch "off" and other switches 81 to 85 is used to select the signal.

In the remote controller 80, there are provided an off switch "off", and a first switch 81 selecting the generation of the intermediate frequency of a first mode waveform, which has a frequency band of 0.6 to 9999 Hz, a voltage of 10 to 47 V and a current of 6.3 to 10.5 mA, for a certain time, a second switch 82 selecting the generation of the intermediate frequency of a second mode waveform, which has a frequency band of 2 to 9999 Hz, a voltage of 9 to 35 V and a current of 6.4 to 10 mA, for a certain time, a third switch 83 selecting the generation of the low frequency of a third mode waveform, which has a frequency band of 2 to 999 Hz, a voltage of 10 to 45 V and a current of 6 to 8.3 mA, for a certain time, a fourth switch 84 selecting the generation of the low frequency of a fourth mode waveform, which has a frequency band of 0.6 to 999 Hz, a voltage of 15 to 58 V and a current of 6 to 10.2 mA, for a certain time, and an AU switch 85 selecting the generation of the low frequency of an electro-acupuncture mode waveform, which has a frequency band of 1 to 999 Hz, a voltage of 25 to 51 V and a current of 6.4 to 10 mA, for 30 minutes. The remote controller 80 allows the user to optionally select five modes by manipulating the above-described switches, and to select a fifth mode capable of repeatedly performing the first and second modes, a sixth mode capable of repeatedly performing the third and fourth modes, and an AU mode capable of repeatedly performing the third and first modes, and the fourth and second modes by pressing the first, third and AU switches 81, 83 and 85 for about 3 minutes, respectively.

By a clock pulse transmitted from an oscillator 432, the microcomputer 430 outputs low and intermediate frequency signals, which are modulated in such a way that the intermediate frequency is carried on the low frequency, to a pulse output terminal.

The modulated low and intermediate frequency signals output through the pulse output terminal is boosted to a voltage of 250 V from 6 V while passing through the frequency adjustment unit 440 formed of a transistor TR2, a resistor R2, a condenser C2 and an inductor L1.

The low and intermediate frequency signals whose voltage is boosted to 250V is alternately output while passing through the frequency output unit 450, which is a flip-flop circuit formed of transistors TR3 to TR6 and resistors R3 to R6.

The low and intermediate frequencies are alternately supplied to the negative and positive electrode plates 50 and 51 through output transistors TR7 and TR8, respectively.

It is made to be known whether the low and intermediate frequencies are output or not, by the flickering of a light emitting diode LED2 connected to the common-contact of the frequency output unit 450, which is a flip-flop circuit.

In the signal detection transistor TR9 of the current detection unit 420 connected to the collector of the transistor TR5, "H" and "L" are repeatedly detected while the low and intermediate frequencies are output, and only "H" is continuously detected when the low and intermediate frequencies are not output. Accordingly, based on the above-described detection of "H" and "L" transmitted to the sensor input terminal (sensor) of the microcomputer 430, the microcomputer 430 can determine whether the electrotherapy apparatus 100 of the present invention is being used while being attached to the human body.

Figure 7:
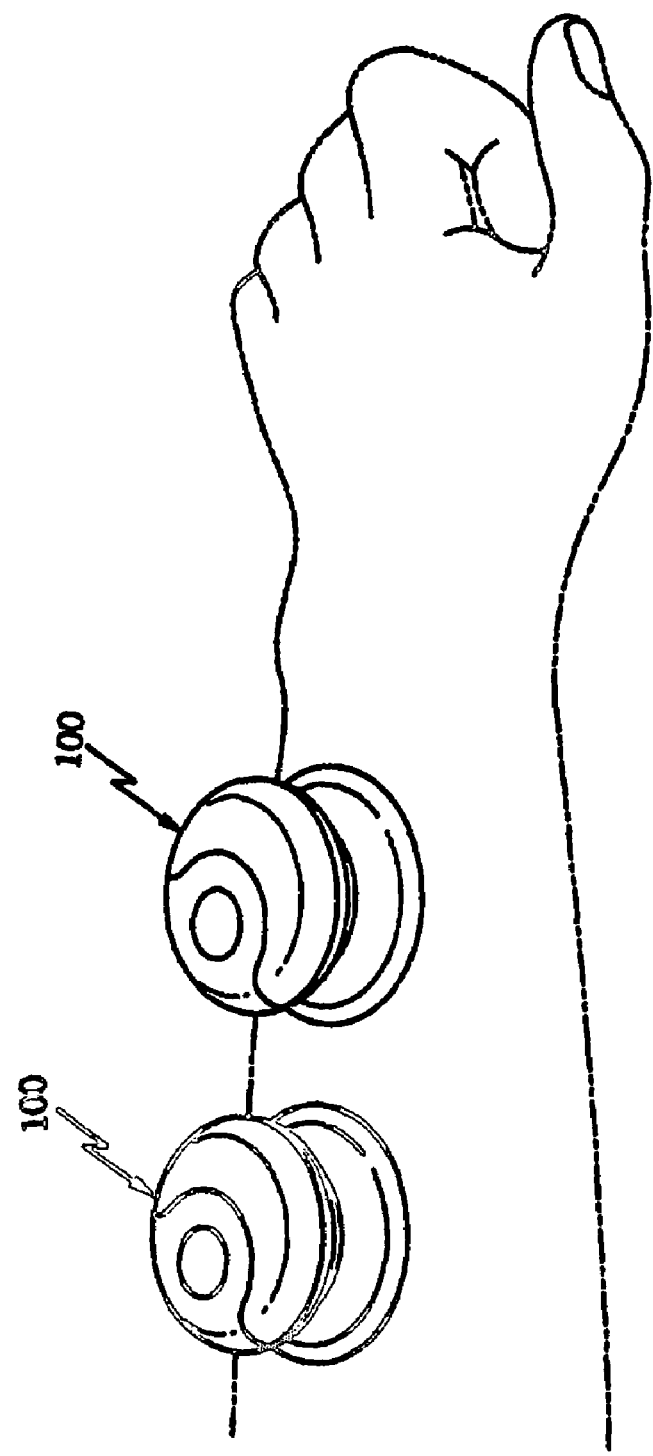
FIG. 7 is a perspective view showing the use of the electrotherapy apparatus of the present invention at the state of being attached to a human body and used.

FIG. 7 is a perspective view showing the use of the electrotherapy apparatus of the present invention at the state of being attached to a human body.

As shown in FIG. 7, a plurality of the electrotherapy apparatuses 100 of the present invention can be used to treat a wide region.

The operation of the electrotherapy apparatus using low and intermediate frequencies according to the present invention is described below.

The electrotherapy apparatus 100 of the present invention is attached to a human body.

When the electrotherapy apparatus 100 of the present invention is applied with a pressure to be attached to a human body, an air is pressurized by a vacuum cup 10 made of a rubber material, and thus the electrotherapy apparatus 100 is attached.

When the electrotherapy apparatus 100 is attached, the pressure of the air causes the contraction of the vacuum cup 10, and the contact terminal 70 is connected to the sensor 41 due to the contraction of the vacuum cup 10.

By bringing the connection terminal 70 into contact with the sensor 41 once, power is supplied to the frequency generator 40 of the electrotherapy apparatus 100, and the frequency generator 40 is in a standby mode in which the frequency generator 40 waits for the control signal of the remote controller 80.

A user can select an output frequency using the remote controller 80. For this purpose, through switches 81 to 85, the remote controller 80 allows the user to optionally select first to fourth modes and an electro-acupuncture mode, which select and output the frequency band of the low and intermediate frequencies, or fifth to eighth modes, which repeatedly perform the first to fourth modes.

The remote controller 80 is provided with an off switch "off" cutting off the power supplied to the frequency generator 40.

That is, In the remote controller 80, there are provided an off switch "off", and a first switch 81 selecting the generation of the intermediate frequency of a first mode waveform, which has a frequency band of 0.6 to 9999 Hz, a voltage of 10 to 47 V and a current of 6.3 to 10.5 mA, for a certain time, a second switch 82 selecting the generation of the intermediate frequency of a second mode waveform, which has a frequency band of 2 to 9999 Hz, a voltage of 9 to 35 V and a current of 6.4 to 10 mA, for a certain time, a third switch 83 selecting the generation of the low frequency of a third mode waveform, which has a frequency band of 2 to 999 Hz, a voltage of 10 to 45 V and a current of 6 to 8.3 mA, for a certain time, a fourth switch 84 selecting the generation of the low frequency of a fourth mode waveform, which has a frequency band of 0.6 to 999 Hz, a voltage of 15 to 58 V and a current of 6 to 10.2 mA, for a certain time, and an AU switch 85 selecting the generation of the low frequency of an electro-acupuncture mode waveform, which has a frequency band of 1 to 999 Hz, a voltage of 25 to 51 V and a current of 6.4 to 10 mA, for 30 minutes. The remote controller 80 allows the user to optionally select five modes by manipulating the above-described switches, and to select a fifth mode capable of repeatedly performing the first and second modes, a sixth mode capable of repeatedly performing the third and fourth modes, and an AU mode capable of repeatedly performing the third and first modes, and the fourth and second modes by pressing the first, third and AU switches 81, 83 and 85 for about 3 minutes, respectively.

When the electrotherapy apparatus 40 is attached to the human body and the low and intermediate frequencies are output from the electrotherapy apparatus 100, a minute current flows through the human body.

When the electrotherapy apparatus 100 is detached from the human body, the minute current does not flow even if the electrotherapy apparatus 100 is being operated.

When the electrotherapy apparatus 100 is detached from the human body, the current detection unit 420 of the frequency generator 40 detects that the minute current does not flow in the transistor TR9 and sends a signal to the sensor input terminal (sensor) of the microcomputer 430, so that the power is cut off and the low and intermediate frequencies are not output any further.

Furthermore, by pressing the off switch of the remote controller 80, the user can cut off the power and set the electrotherapy apparatus 100 in a standby mode.

Through a sensor 41 turned on by the contact terminal 70, a transistor TR1 is turned on while operating power $V_{cc}$ is charged and discharged in and from a condenser C1 while passing through a time-constant device 431 formed of the condenser C1 and a resistor R1.

A single pulse, which has a "L" value only while the transistor TR1 is turned on, is applied to the microcomputer 430, so that the microcomputer 430 is in a standby mode.

In this case, the microcomputer 430 in the standby mode detects whether there is a signal input by the remote controller 80 through the receiving unit 410. If, as a result of the detection, there is no signal input through the receiving unit 410 for 30 seconds, the microcomputer 430 enters a sleep mode to reduce the consumption of a battery 200.

To return to the standby mode from the sleep mode, the contact terminal 70 should be pushed once so that another single pulse is applied to the microcomputer 430.

In the case where the microcomputer 430 is in a standby mode, the microcomputer 430 informs an outside of the state, in which the microcomputer 430 can receive a signal from the remote controller 80, by flickering a light emitting diode LED1.

The microcomputer 430 in the standby mode monitors whether a signal based on the selection of the user is input through the remote controller 80 while being supplied with the power of the battery 200.

By a clock pulse transmitted from an oscillator 432, the microcomputer 430 aware of the selection of the user outputs low and intermediate frequency signals, which are modulated in such a way that the intermediate frequency is carried on the low frequency, to a pulse output terminal.

The modulated low and intermediate frequency signals output through the pulse output terminal is boosted to a voltage of 250 V from a voltage of 6 V while passing through the frequency adjustment unit 440 formed of a transistor TR2, a resistor R2, a condenser C2 and an inductor L1.

The low and intermediate frequency signals whose voltage is boosted to 250 V is alternately output while passing through the frequency output unit 450, which is a flip-flop circuit formed of transistors TR3 to TR6 and resistors R3 to R6.

The low and intermediate frequencies are alternately supplied to the negative and positive electrode plates 50 and 51 through output transistors TR7 and TR8, respectively.

The electrotherapy apparatus using low and intermediate frequencies of the present invention uses a battery as a power source and is operated by a remote controller, and the size thereof is small, so that it is easy to carry the electrotherapy apparatus. Further, as shown in FIG. 5, a plurality of electrotherapy apparatuses can be used according to the portions of treatment and the uses of treatment, so that the range of treatment is considerably wide. Additionally, a user can select a desired frequency band, and thus take required electrotherapy. The electrotherapy apparatus is convenient because the output frequency thereof can be automatically controlled.

INDUSTRIAL APPLICABILITY

As described above, an electrotherapy apparatus using low and intermediate frequencies in accordance with the present invention is useful in that the effect of treatment is increased because the electrotherapy apparatus provides treatment using low and intermediate frequencies, and ill side-effects, such as an allergy and the removal of hairs, are illuminated using conductive rubber, and an attachable pad can be used semi-permanently.

Furthermore, the prevent invention has the effect of a cupping glass, widely used in oriental-medical treatment, using air compression. Additionally, a plurality of electrotherapy apparatuses can be attached to a human body and then a control signal is issued by a remote controller, so that inconvenience caused by wires can be removed and the user can alone simply perform treatment on a wide portion without another person's help.

The invention claimed is:

1. An electrotherapy apparatus using low and intermediate frequencies, comprising:
    a vacuum cup to be attached to a human body;
    a housing connected to an upper portion of the vacuum cup;
    a connection member adapted to connect the vacuum cup and the housing;
    a frequency generator on a printed circuit board that is included in the housing and includes circuits, including a sensor and a microcomputer;
    negative and positive electrode plates contained in the vacuum cup to be supported by springs, and adapted to come in contact with the human body while being operated to ascend and descend;
    connection terminals connected to the frequency generator and the springs to output frequencies to the negative and positive electrode plates;
    a connection terminal located in the vacuum cup to be connected to the sensor so as to operate the frequency generator during treatment; and
    a remote controller adapted to wirelessly control the frequency generator,
        wherein the negative and positive electrode plates are connected to each other through an insulation plate, and include fixation protrusions on which the springs are fixed, respectively and
        wherein the frequency generator comprises:
        a receiving unit receiving a control signal of the remote controller;
        a current detection unit detecting the magnitude of currents and giving notice that the negative and positive electrode plates are detached from the human body;
        a microcomputer cutting off power in response to a signal of the current detection unit, and controlling output frequency and voltage in response to a control signal of the receiving unit;
        a frequency adjustment unit amplifying the low and intermediate frequencies, which are modulated and output in such a way that the intermediate frequency is carried on the low frequency, according to an internal program of the microcomputer; and
        a frequency output unit outputting the low and intermediate frequencies amplified in the frequency adjustment unit,
    wherein:
        the frequency output unit allows the low and intermediate frequencies, which are boosted to a voltage of 250 V while passing through the frequency adjustment unit, to be alternately output while passing through a flip-flop circuit composed of transistors and resistors, and
        the alternately output low and intermediate frequencies pass through output transistors, and then are alternately supplied to the negative and positive electrode plates.

2. An electrotherapy apparatus using low and intermediate frequencies, comprising:

a vacuum cup to be attached to a human body;

a housing connected to an upper portion of the vacuum cup;

a connection member adapted to connect the vacuum cup and the housing;

a frequency generator on a printed circuit board that is included in the housing and includes circuits, including a sensor and a microcomputer;

negative and positive electrode plates and contained in the vacuum cup to be supported by springs and adapted to come in contact with the human body while being operated to ascend and descend;

connection terminals and connected to the frequency generator and the springs and to output frequencies to the negative and positive electrode plates and;

a connection terminal located in the vacuum cup to be connected to the sensor so as to operate the frequency generator during treatment; and a remote controller adapted to wirelessly control the frequency generator, wherein the frequency generator comprises:

a receiving unit receiving a control signal of the remote controller;

a current detection unit detecting the magnitude of currents and giving notice that the negative and positive electrode plates and are detached from the human body;

a microcomputer cutting off power in response to a signal of the current detection unit, and controlling output frequency and voltage in response to a control signal of the receiving unit;

a frequency adjustment unit amplifying the low and intermediate frequencies, which are modulated and output in such a way that the intermediate frequency is carried on the low frequency, according to an internal program of the microcomputer; and a frequency output unit outputting the low and intermediate frequencies amplified in the frequency adjustment unit, and wherein the current detection unit is constructed in such a way that a signal transistor thereof is connected to a collector of the transistor of the frequency output unit, so that "High" and "Low" signal are repeatedly detected while the low and intermediate frequencies are output, only "High" signal is continuously detected while the low and intermediate frequencies are not output, and results of the detection are transmitted to a sensor input terminal (sensor) of the microcomputer.

* * * * *